US011541392B2

(12) United States Patent
Shin

(10) Patent No.: US 11,541,392 B2
(45) Date of Patent: Jan. 3, 2023

(54) APPARATUS FOR TESTING OF PLATELET USING BLOCKAGE PHENOMENON

(71) Applicant: Korea University Research and Business Foundation, Seoul (KR)

(72) Inventor: Se-Hyun Shin, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 344 days.

(21) Appl. No.: 16/098,681

(22) PCT Filed: Feb. 16, 2017

(86) PCT No.: PCT/KR2017/001693
§ 371 (c)(1),
(2) Date: Nov. 2, 2018

(87) PCT Pub. No.: WO2017/191890
PCT Pub. Date: Nov. 9, 2017

(65) Prior Publication Data
US 2020/0269247 A1    Aug. 27, 2020

(30) Foreign Application Priority Data

May 6, 2016 (KR) .......................... 10-2016-0055876

(51) Int. Cl.
*B01L 3/00* (2006.01)
*G01N 33/49* (2006.01)

(52) U.S. Cl.
CPC .... *B01L 3/502761* (2013.01); *G01N 33/4905* (2013.01); *B01L 2200/0647* (2013.01);
(Continued)

(58) Field of Classification Search
CPC ....... B01L 3/502761; B01L 2200/0647; B01L 2300/0861; B01L 2300/12;
(Continued)

(56) References Cited

U.S. PATENT DOCUMENTS 9,260,693 B2* 2/2016 Johnson ................ B01L 3/52
2007/0267336 A1* 11/2007 Ohnishi ............ B01L 3/502753
210/198.2
(Continued)

FOREIGN PATENT DOCUMENTS

KR    10-2011-0056497 A    5/2011
KR      10-1193566 B1    10/2012
(Continued)

OTHER PUBLICATIONS

Hou, HW et al. (2011). "Microfluidic Devices for Blood Fractionation." Micromachines. 2(3): 319-343. (Year: 2011).*
(Continued)

*Primary Examiner* — Matthew D Krcha
*Assistant Examiner* — Jacqueline Brazin
(74) *Attorney, Agent, or Firm* — NSIP Law

(57) ABSTRACT

The present invention relates to a platelet testing device using blockage phenomenon, comprising: a sample chamber containing blood sample; a microfluidic tube which is in fluid communication with the sample chamber and through which the blood sample flows; and a microbead packing arranged on a flow path of the blood sample of the microfluidic tube; wherein the microbead packing comprises: a packing pipe which constitutes a part of the flow path of the blood sample; and a plurality of microbeads contained in the packing pipe and arranged to be in close contact with each other so as to form voids between the microbeads, whereby function of the platelet is tested by blockage phenomenon of the voids due to the platelet in the blood sample which flows through the microfluidic tube from the sample chamber according to the present invention.

17 Claims, 4 Drawing Sheets

(52) U.S. Cl.
CPC ... *B01L 2300/0861* (2013.01); *B01L 2300/12* (2013.01); *B01L 2400/082* (2013.01)

(58) Field of Classification Search
CPC ....... B01L 2400/082; B01L 2300/0681; B01L 2300/0832; B01L 2200/0631; B01L 3/502753; B01L 2300/0883; B01L 3/5027; B01L 2300/0819; B01L 2300/06; B01L 2300/16; G01N 33/4905; G01N 33/49
USPC .......................................................... 422/73
See application file for complete search history.

(56) References Cited

U.S. PATENT DOCUMENTS

| | | | | |
|---|---|---|---|---|
| 2008/0194012 | A1* | 8/2008 | Lee | G01N 15/1459 422/68.1 |
| 2009/0266421 | A1* | 10/2009 | Linder | B01L 3/502784 137/1 |
| 2010/0151465 | A1* | 6/2010 | Ju | C12Q 1/6816 435/6.12 |
| 2012/0309004 | A1* | 12/2012 | Hwang | B01L 3/502753 435/6.11 |
| 2014/0038193 | A1* | 2/2014 | Spoto | B01L 3/5027 435/6.12 |
| 2015/0338424 | A1* | 11/2015 | Shin | G01N 15/1484 436/63 |

FOREIGN PATENT DOCUMENTS

| | | | |
|---|---|---|---|
| KR | 10-2014-0094036 A | 7/2014 | |
| KR | 10-2015-0124895 A | 11/2015 | |
| WO | WO-0234197 A2 * | 5/2002 | ............ B01L 3/0293 |
| WO | WO-2004081541 A1 * | 9/2004 | ....... G01N 33/54386 |
| WO | WO-2012016136 A2 * | 2/2012 | ........ B01L 3/502707 |
| WO | WO-2015193478 A1 * | 12/2015 | ............... B03D 3/00 |

OTHER PUBLICATIONS

Song, Suk-Heung, et al., "Migration distance-based platelet function analysis in a microfluidic system", *Biomicrofluidics*, 2013, pp. 1-10, vol. 7 (12 pages in English).

International Search Report dated Jun. 13, 2017 in corresponding International Application No. PCT/KR2017/001693 (2 pages in English, 2 pages in Korean).

* cited by examiner

APPARATUS FOR TESTING OF PLATELET USING BLOCKAGE PHENOMENON

CROSS REFERENCE TO RELATED APPLICATION(S)

This application is a U.S. national stage application of International Application No. PCT/KR2017/001693 filed on Feb. 16, 2017, which claims the benefit of Korean Patent Application No. 10-2016-0055876 filed on May 6, 2016, in the Korean Intellectual Property Office.

TECHNICAL FIELD

The present invention relates to an apparatus for testing platelet using blockage phenomenon and in particular to an apparatus for testing platelet using blockage phenomenon by which it is possible to test characteristics of the platelet based on a phenomenon which blocks a flow path by attachment or aggregation of activated platelets.

BACKGROUND ART

Platelet tests are widely used as congenital platelet function abnormality or pre-operative screening tests, and are particularly important for differentiating hemorrhagic diseases caused by congenital or acquired platelet function abnormalities among hemorrhagic diseases having no platelet numerical abnormalities.

Recently, such platelet function tests have come to be widely used to test for increased hemorrhagic tendency as an effect of an anti-platelet drug, which is used for the treatment and prevention of cardiovascular diseases, or to test for resistance to a drug.

A bleeding time (BT) test is a bleeding-time measurement test that was developed about 100 years ago and has been used as a platelet function screening test to date. However, there are problems in that the platelet function test currently in use is difficult to standardize, has low clinical usefulness, and requires the use of an invasive method. Accordingly, an objective measurement method for measuring the platelet function is required.

In the case of a platelet function analyzer (e.g.: PFA-100), which is designed to solve the above-described problems and which is used as a technique for measuring the platelet function, in order to measure the characteristic of aggregation of platelets caused by a von Willebrand factor (vWF) activated at a high shear rate, the clogging time that is required for clogging of orifice holes of an orifice, which is coated with collagen, adenosine diphosphate (ADP), or epinephrine, due to aggregation of platelets after enabling whole blood to flow through a long capillary at a high shear rate is measured using a pressure or a flow rate.

In order to perform the platelet function test, it is inevitable to depend on the function of the vWF, the test is dependent on the hematocrit (Hct), and the anti-platelet or anti-clopidogrel test cannot be performed, which are considered to be drawbacks. Further, there is a drawback in that testing costs are increased due to the necessity of a two-stage test process for the platelet function test.

In particular, blood samples must be exposed at a high shear rate for a predetermined period of time or longer in order to activate the vWF. For this purpose, PFA-100 adopts a method of enabling blood to rapidly flow through a very long capillary. However, this method has problems in that a large amount of blood is required and that the vWF located at the center of the tube, at which the shear rate is a minimum, is not activated even though the vWF located near the capillary wall, at which the shear rate is a maximum, is easily activated. This may cause a problem in the repeatability of the test result.

In order to solve the above-described problems, Korean Patent Registration No. 10-1193566 proposes a micro-chip-based platelet multifunction testing device. The device includes a sample storage chamber in which a blood sample is received, an stirrer provided in the sample storage chamber to induce a shear flow in the blood sample, parallel channels provided to form a plurality of paths through which the blood stirred using the stirrer flows, a vacuum device connected to the ends of the parallel channels to enable the stirred blood to flow through the parallel channels while maintaining a constant pressure, a light source provided at the rear end of the parallel channels to radiate light to the parallel channels, and an image sensor which receives the light transmitted through the blood in the parallel channels and which converts the light into an electrical signal, thus measuring the flow rate of blood. Accordingly, it is possible to test a plurality of platelet functions by a single test, and an effect of not only reducing the test time but also reducing the testing costs is provided.

However, as shown in FIG. 1, a micro-chip-based platelet multifunction testing device disclosed in the above Korean Patent Registration is generally configured to have a chip having a channel in which blood flows by attaching a top plate to a bottom plate having a channel pattern. In this regard, since the height (h) of the channel is very fine, a minor error during the manufacturing of the channel disadvantageously causes the height of the channel to be non-uniform.

Such problem decreases the reliability of the platelet test since the same result, i.e., the same stop distance, is not obtained even for the platelet function test having the same blood sample or the same characteristics.

Further, a micro-chip-based platelet multifunction testing device disclosed in the above Korean Patent Registration has micro fillers (12, see FIG. 1) to which platelets are attached or beads 54 in the channel. As shown in FIG. 1, a lot of platelets which are not attached pass through an area (see area 'A' in the FIG. 1) above the micro filler 12 or beads 54, or an area between the micro filler 12 and the beads 54, thereby disadvantageously much blood is substantially needed for the channel clogging or the blockage phenomenon is not expected.

DISCLOSURE

Technical Problem

Accordingly, the present invention is provided to solve the above problems and an object of the present invention is to provide a platelet testing device using blockage phenomenon which makes it possible to substantially generate blockage phenomenon with a small amount of blood sample when function of platelets is tested using blockage phenomenon.

Also, another object of the present invention is to provide a platelet testing device using blockage phenomenon which can enhance the reliability of the platelet test by maintaining a gap of a channel through which platelets flow, i.e., a gap in an area where blockage occurs due to the attachment and aggregation of platelets, for each device.

Technical Solution

The above object is accomplished by a platelet testing device using blockage phenomenon, comprising: a sample chamber containing blood sample; a microfluidic tube which is in fluid communication with the sample chamber and through which the blood sample flows; and a microbead packing arranged on a flow path of the blood sample of the microfluidic tube; wherein the microbead packing comprises: a packing pipe which constitutes a part of the flow path of the blood sample; and a plurality of microbeads contained in the packing pipe and arranged to be in close contact with each other so as to form voids between the microbeads, whereby function of the platelet is tested by blockage phenomenon of the voids due to the platelet in the blood sample which flows through the microfluidic tube from the sample chamber according to the present invention.

Here, a size of the void may depend on a size of the microbead, and the void may be configured to have a size by which erythrocyte in the blood sample can pass through the void and by which the blockage phenomenon of the void can occur by the attachment of the platelet to the microbead and the aggregation of the platelet.

Also, the size of the microbead may be set such that the size of the void is 3 μm to 40 μm.

Further, the microbead may be coated with clogging accelerant material which facilitates the attachment of the platelet.

Here, the clogging accelerant material may comprise any one among agonists including collagen, fibrinogen, adenosine diphosphate (ADP), epinephrine, arachidonic acid, thromboxane A2, thrombin, and iso-thrombin-receptor-activating peptide (iso-TRAP), or a combination thereof.

Also, the platelet in the blood sample may be configured to flow into the microbead packing in an activated state in the sample chamber.

Here, the platelet testing device using blockage phenomenon may further comprise a stirrer rotatably arranged in the sample chamber to apply shear force to the blood sample so as to activate the platelet in the blood sample.

Further, a platelet activating reagent which activates the platelet in the blood sample may be contained in the sample chamber, whereby the platelet is activated in the sample chamber.

Also, a degree to which the platelet is activated can be determined by any one of a travel distance of the blood sample which passed through the microbead packing and time taken for a stop of the blood sample flow, based on at least one of whether the void is blocked, a degree of the blockage of the void, and time taken for the void blockage, according to a degree to which the platelet in the blood sample is activated.

Also, the microfluidic tube and the microbead packing may be provided to have a plurality of microfluidic tubes and a plurality of microbead packings, and wherein a plurality of testing channels are formed in such a manner that each test channel is formed by one microfluidic tube and one microbead packing.

Also, one of the plurality of test channels may form a control channel and the other of the plurality of test channels may form a sample channel, wherein a platelet flowing into the microbead packing of the control channel flows into the microbead packing in a non-activated state and a platelet flowing into the microbead packing of the sample channel flows into the microbead packing in an activated state.

Also, the platelet testing device may further comprise a stirrer rotatably arranged in the sample chamber of the sample channel to apply shear force to the blood sample so as to activate the platelet in the blood sample.

Also, a platelet activating reagent which activates the platelet in the blood sample may be contained in the sample chamber, whereby the platelet is activated in the sample chamber.

Here, the platelet activating reagent may comprise any one of calcium ion, adenosine diphosphate (ADP), epinephrine, arachidonic acid, thromboxane A2, thrombin, and iso-thrombin-receptor-activating peptide (iso-TRAP), or a combination thereof.

Also, the microbead packing may further comprise a mesh member which is arranged at a rear end of the packing pipe in a flow direction of the blood sample to prevent loss of the microbeads.

Also, at least one part of surface of the microbead may be shaped to be porous.

Also, the microbeads which are in close contact with each other may be maintained in a state of being fused each other by a heat-fuse process.

Also, the platelet testing device may further comprise a negative pressure inflow chamber which is connected to the microfluidic tube at an opposite of the sample chamber and which introduces a negative pressure from outside such that the blood sample flows through the microfluidic tube.

Also, a degree of an activation of the platelet may be determined based on at least one of travel distance of the blood sample in the sample channel, travel distance of the blood sample in the control channel, time taken for the stop of the blood sample in the sample channel, and time taken for the stop of the blood sample in the control channel, a difference of travel distance of the blood sample in the sample channel and travel distance of the blood sample in the control channel, a ratio of travel distance of the blood sample in the sample channel to travel distance of the blood sample in the control channel, a difference of time taken for the stop of the blood sample in the sample channel and time taken for the stop of the blood sample in the control channel, and a ratio of time taken for the stop of the blood sample in the sample channel to time taken for the stop of the blood sample in the control channel.

Also, an inner diameter of the packing pipe may be configured to be the same as an inner diameter of the microfluidic tube.

Also, the microbead packing may have a length of 1 mm to 2 mm in a flow direction.

Advantageous Effects

With the above arrangement, the present invention provides a platelet testing device using blockage phenomenon which can substantially generate blockage phenomenon with a small amount of blood sample when function of platelets is tested using blockage phenomenon.

Also, the reliability of the platelet test can be enhanced by maintaining a gap of a channel through which platelets flow, i.e., a gap in an area where blockage occurs due to the attachment and aggregation of platelets, for each device.

Figure 1:
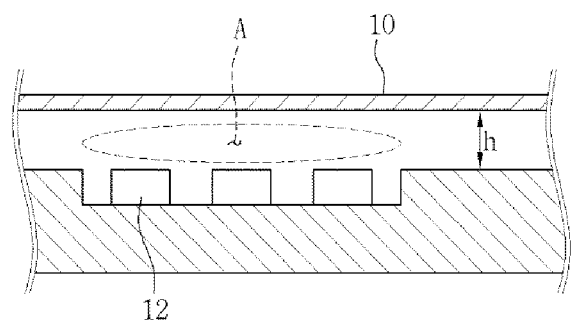
FIG. 1 shows a view describing a micro-chip-based platelet multifunction testing device according to a prior art.

EXPLANATION OF REFERENCE NUMBER 100,200: platelet testing device
110,110a,110b: sample chamber
120,120a,120b: microfluidic tube
130,130a,130b: microbead packing
131: packing pipe
132: microbeads
133: mesh member
140,140a,140b: pressure inflow chamber
150,150a,150b: stirring device

BEST MODE

The present invention relates to a platelet testing device using blockage phenomenon, comprising: a sample chamber containing blood sample; a microfluidic tube which is in fluid communication with the sample chamber and through which the blood sample flows; and a microbead packing arranged on a flow path of the blood sample of the microfluidic tube; wherein the microbead packing comprises: a packing pipe which constitutes a part of the flow path of the blood sample; and a plurality of microbeads contained in the packing pipe and arranged to be in close contact with each other so as to form voids between the microbeads, whereby function of the platelet is tested by blockage phenomenon of the voids due to the platelet in the blood sample which flows through the microfluidic tube from the sample chamber according to the present invention.

MODE FOR INVENTION

Hereinafter, embodiments of the present invention will be described in detail with reference to the accompanying drawings.

Figure 2:
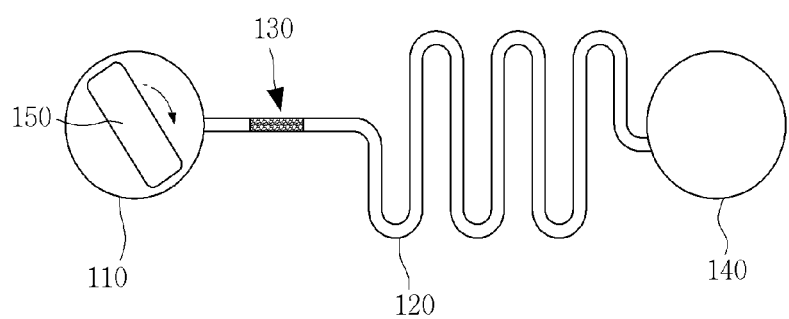
FIG. 2 is a view illustrating a platelet testing device using blockage phenomenon according to one embodiment of the present invention.

FIG. 2 is a view illustrating a structure of a platelet testing device 100 using blockage phenomenon according to one embodiment of the present invention.

Referring to FIG. 2, the platelet testing device 100 according to one embodiment comprises a sample chamber 110, a microfluidic tube 120, and a microbead packing 130.

The sample chamber 110 contains a blood sample. In FIG. 2, the sample chamber 110 has a substantially circular shape, but it is noted that the structure or shape of the sample chamber is not limited thereto. Here the size of the sample chamber 110 may vary depending on the purpose of use, and the sample chamber may be formed of an optically transparent material so as to easily observe the inside of the sample chamber from the outside.

In the embodiment of the present invention, the blood sample contained in the sample chamber 110 may be a full blood, but it should be noted that the blood sample may be a thrombocyte-rich blood plasma from which erythrocyte and leukocyte are removed.

A microfluidic tube 120 is connected to the sample chamber 110 at one end and the blood sample in the sample chamber 110 flows through the microfluidic tube 120 connected to the sample chamber 110. Here, the microfluidic tube 120 may be formed of various material such as rubber, plastic, or glass.

In one embodiment, for example, the microfluidic tube 120 is connected to a pressure inflow chamber 140 at the other end of the pipe. The pressure inflow chamber 140 is connected to a negative pressure application device and a negative pressure from the negative pressure application device is applied by the pressure inflow chamber 140 so that flow of the blood sample is induced through the microfluidic tube 120.

A microbead packing 130 is arranged on a flow path of the blood sample of the microfluidic tube 120. In one example, the microbead packing 130 is inserted into the microfluidic tube 120, in particular into a location, as shown in FIG. 2 so as to be arranged on a flow path. Alternatively, microfluidic tubes 120 are inserted into both end portions of the microbead packing 130, respectively so as to connect the pipes to the microbead packing, thereby the microbead packing 130 being installed on a flow path of the blood sample. With the above arrangement, the blood sample contained in the sample chamber 110 flows into the front end of the microfluidic tube 120, passes through the microbead packing 130, and then flows again through the microfluidic tube 120.

Hereinafter, referring to FIGS. 3 and 4, a structure of microbead packing 130 of a platelet testing device 100 according to one embodiment of the present invention will be described in detail.

Figure 3:
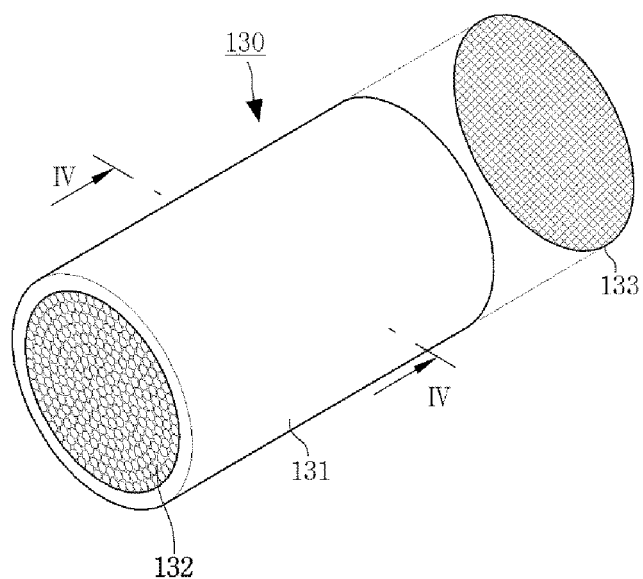
FIG. 3 is a view illustrating a microbead packing of a platelet testing device using blockage phenomenon according to one embodiment of the present invention.
Figure 4:
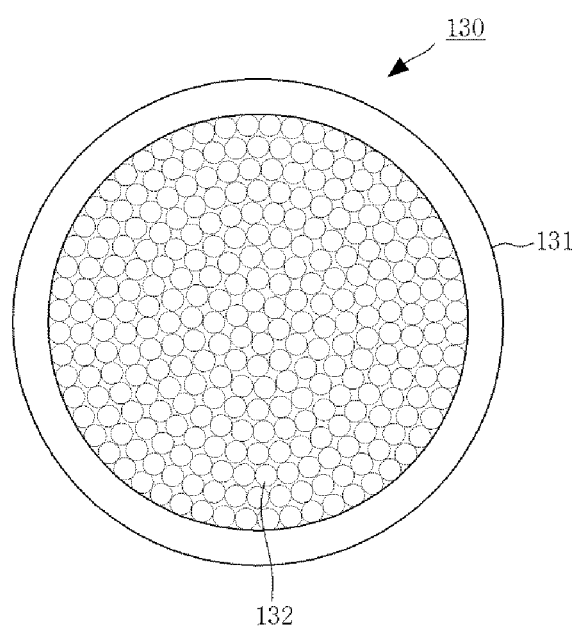
FIG. 4 is a cross-sectional view taken along a line IV-IV of FIG. 3.

According to one embodiment of the present invention, as shown in FIGS. 3 and 4, the microbead packing 130 comprises a packing pipe 131 and microbeads 132.

The packing pipe 131 constitutes a part of a flow path of the blood sample. In case that the microbead packing 130 is inserted into the microfluidic tube 120 to form a part of the flow path as explained above, the packing pipe 131 in which microbeads 132 are packed may be inserted into the microfluidic tube 120.

Also, in case that microfluidic tubes 120 are connected to both ends of the microbead packing 130, both ends of the packing pipe 131 may be inserted into each of the microfluidic tubes 120 so as to form a part of the flow path. Here, the packing pipe 131 may be formed of various material such as rubber or plastic.

Here, in one example, the inner diameter of the packing pipe 131 may be identical to the inner diameter of the microfluidic tube 120. Accordingly, a flow variance caused by the inconsistency of the inner diameter of the microfluidic tube 120 and the inner diameter of the packing pipe 131 can be minimized and the reliability of blockage time of the micro packing 130 which will be described below can be increased by the identical inner diameters. Here, the expression 'identical' is not intended to mean that the inner diameter of the packing pipe 131 is numerically identical to the inner diameter of the microfluidic tube 120. Although there is a numerical difference by an error, etc., such a difference may be ignored if the inner diameters can be regarded as being substantially the same by those skilled in the art.

Microbeads 132 are contained in the packing pipe 131 such that microbeads are closely adhered to each other. The close adhesion generates voids which are three-dimensional space between the microbeads 132. Here, the microbeads 132 may be formed of various material such as glass, plastic, etc.

Also, the microbead packing 130 may comprise a mesh member 133 which is arranged at a rear end of the packing pipe 131 in a flow direction of the blood sample so as to prevent loss of microbeads 132. In FIG. 3, the mesh member 133 is in the form of a mesh, but it should be noted that the shape thereof is not limited thereto if the loss of the microbeads 132 can be prevented.

Further, the mesh member 133 may be arranged at the front end of the packing pipe 131. Here, it is advantageous that void of the mesh member 133 is configured to have a size which does not allow the microbeads 132 to pass through the void and which does not influence the test.

In alternative embodiment, in order to prevent the loss of the microbeads 132, microbeads 132 adjacent to each other may be maintained in a state of being fused each other by a heat-fuse process. That is, during the manufacturing of the microbead packing 130, if the microbeads 132 are heat-fused in a packed state, contact portions where the microbeads 132 are adjacent to each other are fused, thereby preventing respective microbead 132 from being lost in the packing pipe 131 of the microbead packing 130, and also thereby connecting the entire microbeads 132 to be an integral element to prevent the loss of the entire microbeads 132. Here, a process to coat clogging accelerant material, which will be described below and is coated on the microbeads 132, may be carried out after the heat fuse process.

Figure 5:
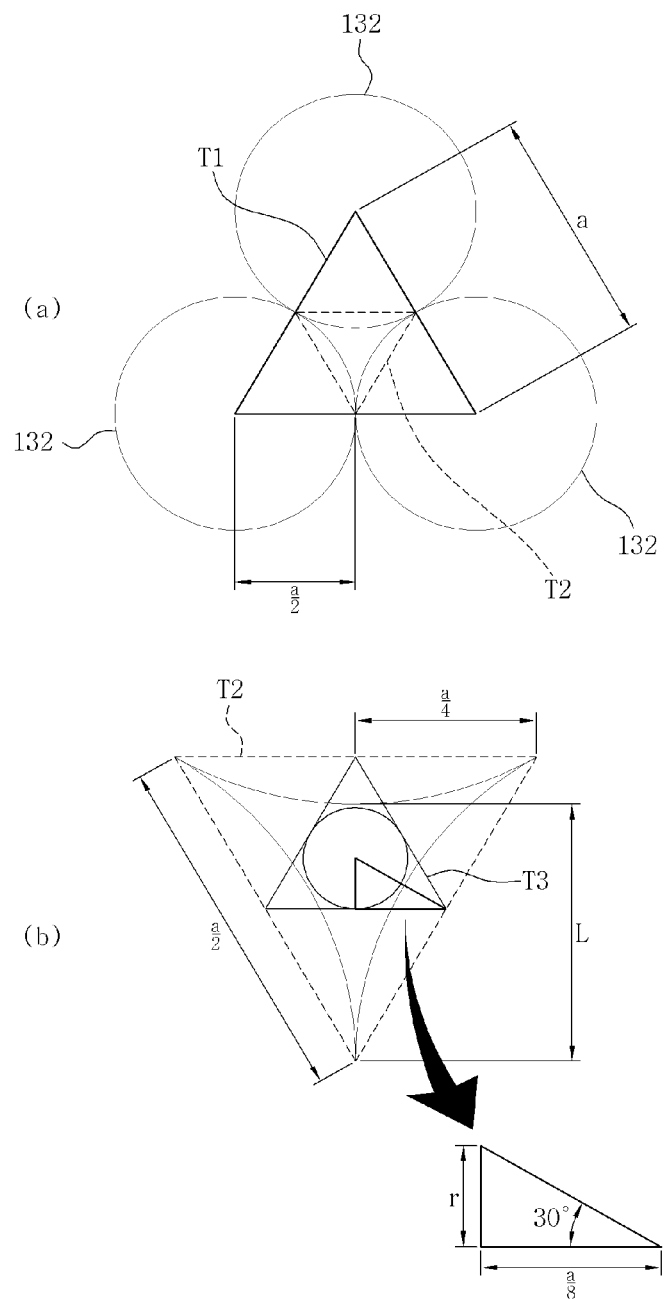
FIG. 5 is a view describing a size of microbead or void of a platelet testing device using blockage phenomenon according to one embodiment of the present invention.

Meanwhile, the size of the void according to the present invention is determined depending on the size of the microbeads 132. Referring to FIG. 5, FIG. 5(a) shows an example of a void formed by three microbeads 132. One equilateral triangle T1 is formed by connecting centers of the three microbeads to each other and the length a of one side of the triangle is the same as the diameter of the microbead 132. Further, a equilateral triangle T2 is formed if centers of each side of the triangle T1 are connected to each other, and the length of a side of the triangle T2 is a/2.

FIG. 5(b) is an enlarged view of the equilateral triangle T2. Referring to FIG. 5(b), if centers of each side of the triangle T2 are connected to each other, an equilateral triangle T3 is formed and the length of a side of the triangle T3 is a/4.

Here, the length L of a void formed by the close contact of the three microbeads 132 is calculated by a height of the triangle T3 and a diameter of a circle in the triangle T3, and the diameter of the circle is calculated by a height r of a right-angled triangle which is shown by an enlarged view.

As such, the size of void depends on the size of the microbeads 132 and in turn, the size of the microbeads 132 is determined to form a desired size of the void. In the embodiment of the present invention, the void is configured to have a size by which erythrocyte in the blood sample is able to pass through the void and by which platelets are adhered to the microbeads 132 and then are aggregated, thereby generating blockage phenomenon of the voids.

That is, the lower limit of the void size is determined such that the void is not clogged with erythrocyte and thus erythrocyte is able to pass through the void. The upper limit of the void size is determined such that the void is clogged by the attachment of platelet to microbeads 132 near the void or by the aggregation of platelets. In the embodiment, the size of the microbeads is set such that the size of the void is 3 µm to 40 µm.

In a test using the platelet testing device 100 according to one embodiment, the microbead packing 130 was configured to make the void have the size of 133 µm by making the microbead 132 have the size of 400 µm, and then the blood sample was tested to flow through the microfluidic tube (120) from the sample chamber 110. This test resulted in that a void whose size is more than 133 µm has a problem with a chip-based-testing device of prior art, i.e., a non-clogging problem.

Accordingly, it was confirmed that if the void is large, the platelets pass through the void even when the platelets are attached to the microbeads 132 or to each other, so that the blockage phenomenon of the void does not happen and in turn, problems of the prior chip-type testing device are be solved.

Also, by a test, it is confirmed that a void blockage phenomenon happened when the size of the void is 3 µm to 40 µm. Also, it is confirmed that it is possible to perform a platelet test using a platelet testing device 100 according to the present invention even for the void having a size of 40 µm if the microbeads 132 are coated with the clogging accelerant material.

Therefore, it is advantageous that the size of the void according to the embodiment is 3 µm to 40 µm, as described above.

Also, the length of the microbead packing 130 in a flow direction may influence a blockage time of the microbead packing 130. In one embodiment, for example, the length of the microbead packing is set to be 1 mm to 2 mm.

Meanwhile, leukocyte in the blood sample is relatively bigger than platelet or erythrocyte, but is relatively fewer than platelet or erythrocyte. Therefore, it is confirmed by test that a blockage by leukocyte in the microbead packing 130 does not happen. Accordingly, in the embodiment, when it comes to the determination of the void size, the size of leukocyte is ignored.

Also, in the embodiment, for example, microbeads 132 are coated with a clogging accelerant material which facilitates attachment of the platelet. The clogging accelerant material may be any one among agonists including collagen, fibrinogen, adenosine diphosphate (ADP), epinephrine, arachidonic acid, thromboxane A2, thrombin, and iso-thrombin-receptor-activating peptide (iso-TRAP), or a combination thereof.

Meanwhile, in the embodiment of the present invention, for example, the platelet in the blood sample is activated in the sample chamber 110 and then flows into the microbead packing 130 in an activated state. The platelet is activated in the sample chamber 110 by a physical method, a chemical method, or a combination thereof.

For example, the platelet testing device 100 according to the embodiment of the present invention may comprise a stirrer 150 which is rotatably installed in the sample chamber 110, as shown in FIG. 2. The stirrer 150 may be formed of magnetic material or magnetisable material to rotate in the sample chamber 110 by means of a magnet which rotates outside the sample chamber 110. Accordingly, if the stirrer 150 rotates in the sample chamber 110, shear force is applied to the blood sample to activate the platelet. Here, for example, the stirrer 150 may rotate at a speed of 2500 rpm to apply shear force by which the platelet can be activated.

Accordingly, based on the activation of the platelet in the sample chamber 110 by the stirrer 150, the blockage phenomenon at the microbead packing 130, i.e., a flow travel distance by which the blood sample travels until a blockage phenomenon occurs in the microbead packing 130 or time taken for the blockage phenomenon, is measured, and thus it is possible to identify whether the platelet is activated or how the platelet is activated, whereby the platelet testing device 100 can be applied to the platelet function test.

In a chemical method, a platelet activating reagent for activating platelet in the blood sample may be provided in the sample chamber 110. The platelet activating reagent may be introduced together with the blood sample, or may be coated on an inner wall surface of the sample chamber 110, so that the reagent reacts with the platelet. In the embodiment, the platelet activating reagent may be any one of calcium ion, adenosine diphosphate (ADP), epinephrine, arachidonic acid, thromboxane A2, thrombin, and iso-thrombin-receptor-activating peptide (iso-TRAP), or a combination thereof.

By the above chemical method, it is possible to check whether the platelet is activated after the reaction with the platelet activating reagent and it is possible to perform a drug reaction test for a patient who is taking an anti-platelet agent such as aspirin, clopidogrel, Reopro, etc. In this case, when a stirrer 150 installed in the sample chamber 110 is operated, the stirrer can be controlled to apply a rotation or shearing force to such a degree that the platelet activating reagent and the platelet are mixed without activating the platelet.

With the above arrangement, the blood sample flowing through the microfluidic tube 120 from the sample chamber 110 is supposed to pass through voids between the microbeads 132 of the microbead packing 130 during the flow, and the platelet function test can be made by the blockage phenomenon of the void caused by the platelet in the blood sample, i.e., the activated platelet.

Here, in a platelet test, at least one of whether the void is blocked, a degree of the blockage of the void, and time taken for the void blockage depends on a degree to which the platelet in the blood sample is activated, which influences any one of a travel distance of the blood sample which passed through the microbead packing 130 and time taken for the stop of the blood sample determines, and a degree of the activation of the platelet is determined according to the travel distance or the time.

For example, in case of a blood sample of a person having very active platelets, the microbead packing 130 is blocked more faster for the same void size, so that the blood sample travels by a shorter distance and then stops and also, time taken for the stop of flow will be shorter. Meanwhile, in case that a blood sample has platelets whose function is lowered for the same void size, it takes more time for the microbead packing 130 to be blocked or there is no blockage and thus, travel distance will become relatively longer. This difference makes it possible to test the platelet.

Further, if area to be blocked by aggregation and attachment of the platelet is formed by voids generated by the close adhesion of microbeads 132 and a size of the voids remains constant, a reliability of the test will increase and it will be possible to make a flow path for the blockage phenomenon more easily than a channel made by previous chip-based testing devices.

Also, since voids formed by microbeads 132 are used, a size of the void can be adjusted by a diameter of the microbead 132 and it is possible to provide a void by which blockage phenomenon substantially can occur, so that a test can be made with a small amount of blood sample.

Hereinafter, referring to FIG. 6, a platelet testing device 200 according to another embodiment will be described. Here, in the embodiment of FIG. 6, there are a plurality of sample chambers 110a, 110b, a plurality of microfluidic tubes 120a, 120b, and a plurality of microbead packings 130a, 130b, and a plurality of testing channels are formed in such a manner that each test channel is formed by one sample chamber 110a, 110b, one microfluidic tube 120a, 120b, and one microbead packing 130a, 130b.

Figure 6:
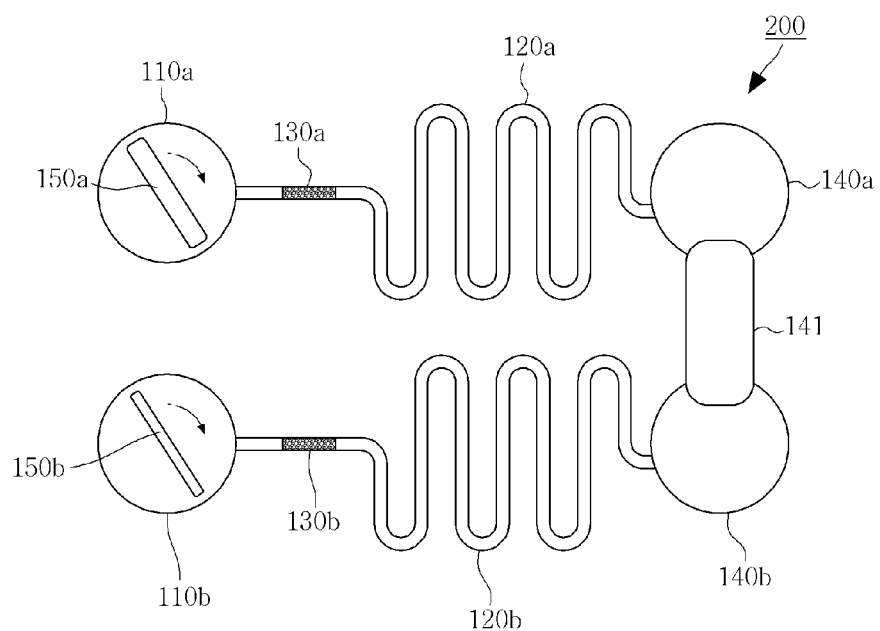
FIG. 6 is a view illustrating a structure of a platelet testing device using blockage phenomenon according to one embodiment of the present invention.

The platelet testing device 200 according to another embodiment comprises a plurality of test channels and in an example of FIG. 6, there are two test channels.

Here, one channel of the plurality of test channels may form a control channel 110a, 120a, 130a, 140a, 150a and the other channel may form a sample channel 110b, 120b, 130b, 140b, 150b. In this case, platelets flowing into the microbead packing 110a of the control channel 110a, 120a, 130a, 140a, 150a may be not in an activated state and platelets flowing into the microbead packing 103b of the sample channel 110b, 120b, 130b, 140b, 150b may be in an activated state. Here, the activation of the platelet can be made by a physical method and/or a chemical method as described above. For example, a stirrer 150b can be arranged in the sample chamber 110b of the sample channel 110b, 120b, 130b, 140b, 150b to apply shear force by which the platelet can be activated, or platelet activation reagents can be provided therein.

FIG. 6 shows that a stirrer 150a is arranged in the sample chamber 110a of the control channel 110a, 120a, 130a, 140a, 150a, but the stirrer 150a of the sample chamber 110a of the control channel 110a, 120a, 130a, 140a, 150a may be configured to rotate and perform a stirring function to such a degree that the platelets are not activated.

With the above arrangement, the flow of the blood sample happens simultaneously at the control channel 110a, 120a, 130a, 140a, 150a and at the sample channel 110b, 120b, 130b, 140b, 150b, and it is possible to make a test of the platelet in the blood sample by comparing the travel distance of the blood sample and time taken for the stop of the blood sample flow of the control channel 110a, 120a, 130a, 140a, 150a with those of the sample channel 110b, 120b, 130b, 140b, 150b.

More particularly, blood viscosity, hemagglutination, red blood cell deformability, platelet level, etc. depend on individuals and the measurement of an absolute value of travel distance and time taken for the flow stop based on one test channel will cause an error. The error based on individuals can be compensated to determine the activation of the platelet more correctly by using the difference of travel distance of the blood sample in the control channel 110a, 120a, 130a, 140a, 150a and travel distance of the blood sample in the sample channel 110b, 120b, 130b, 140b, 150b and by using the difference of time taken for the flow stop of the blood sample in the control channel 110a, 120a, 130a, 140a, 150a and time taken for the flow stop of the blood sample in the sample channel 110b, 120b, 130b, 140b, 150b.

Also, it is possible to determine a degree of the activation by using a ratio of travel distance of the blood sample in the control channel 110a, 120a, 130a, 140a, 150a to travel distance of the blood sample in the sample channel 110b, 120b, 130b, 140b, 150b and by using a ratio of time taken for the flow stop of the blood sample in the control channel 110a, 120a, 130a, 140a, 150a to time taken for the flow stop of the blood sample in the sample channel 110b, 120b, 130b, 140b, 150b.

Besides, for the test of the characteristics of platelets, travel distance or time taken for the flow stop of the blood sample in the sample channel 110b, 120b, 130b, 140b, 150b, or travel distance or time taken for the flow stop of the blood sample in the control channel 110a, 120a, 130a, 140a, 150a can be used, respectively.

As shown in FIG. 6, in an example of the above embodiment, each sample chamber 110a, 110b constitutes each test channel, i.e., a control channel 110a, 120a, 130a, 140a, 150a and a sample channel 110b, 120b, 130b, 140b, 150b. Alternatively, it should be noted that a plurality of microfluidic tubes and microbead packings which are diverged from one sample chamber may form each test channel, respectively.

In the embodiment of FIG. 6, for example, pressure inflow chambers 140a, 140b are provided to correspond to each test channel. Here, one negative pressure applying device is configured to apply negative pressure by means of a connecting part 141 which connecting the pressure inflow chambers 140a, 140b to each other such that one negative pressure applying device can apply the same negative pressure to each pressure inflow chamber 140a, 140b. Also, an end of each microfluidic tube may be connected to one pressure inflow chamber and negative pressure may be provided to the corresponding pressure inflow chamber.

In the embodiments described above, for example, microbeads 132 are provided in the form of a sphere. But, microbeads 132 may be configured in such a manner that at least some portion of the microbeads has a porous shape to enhance the attachment of the platelets.

Although several embodiments of the present invention are illustrated and explained above, it is obvious that the embodiments can be easily devised by those skilled in the technical idea of the present invention within the scope of the technical idea or spirit included in the specification of the present invention. The scope of the present invention will be determined by attached claims and their equivalents.

INDUSTRIAL APPLICABILITY

The present invention is applied to the field of testing function of a platelet in a blood.

The invention claimed is:

1. A platelet testing device using blockage phenomenon, comprising:
a sample chamber containing a blood sample;
a microfluidic tube, which is in fluid communication with the sample chamber and through which the blood sample flows; and
a microbead packing arranged on a flow path of the blood sample of the microfluidic tube;
wherein the microbead packing comprises:
a packing pipe disposed in a portion of the microfluidic tube, separated from the sample chamber by the microfluidic tube, and constituting a part of the flow path of the blood sample; and
a plurality of microbeads contained in the packing pipe and arranged to be in close contact with each other so as to form voids between the plurality of microbeads,
whereby function of a platelet is tested by blockage phenomenon of the voids due to the platelet in the blood sample, which flows through the microfluidic tube from the sample chamber,
wherein the packing pipe is extended in parallel with an extension direction of the microfluidic tube and both ends of the packing pipe are connected to the microfluidic tube, and
wherein an inner diameter of the packing pipe is configured to be the same as an inner diameter of the microfluidic tube,
wherein the platelet in the blood sample is configured to flow into the microbead packing in an activated state in the sample chamber,
wherein a degree, to which the platelet is activated, is determined by any one of a travel distance of the blood sample, which passed through the microbead packing, and time taken for a stop of the blood sample flow, based on at least one of whether the void is blocked, a degree of the blockage of the void, and time taken for the void blockage, according to a degree to which the platelet in the blood sample is activated,
wherein at least some of the plurality of microbeads are connected with another microbead adjacent to the at least some of the plurality of microbeads to form a plurality of fused microbeads by a fused portion of the at least some of the plurality of the microbeads and the another microbead, and
wherein the plurality of microbeads are coated with clogging accelerant material, which facilitated attachment of the platelet.

2. The platelet testing device using blockage phenomenon according to claim 1, wherein a size of the void depends on sizes of the plurality of microbeads and the plurality of fused microbeads, and the void is configured to have a size by which erythrocyte in the blood sample can pass through the void and by which the blockage phenomenon of the void can occur by attachment of the platelet to the plurality of microbeads and aggregation of the platelet.

3. The platelet testing device using blockage phenomenon according to claim 1, wherein the size of one of the plurality of microbeads is set such that the size of the void is 3 μm to 40 μm.

4. The platelet testing device using blockage phenomenon according to claim 1, wherein the clogging accelerant material comprises any one among agonists including collagen, fibrinogen, adenosine diphosphate (ADP), epinephrine, arachidonic acid, thromboxane A2, thrombin, and iso-thrombin-receptor-activating peptide (iso-TRAP), or a combination thereof.

5. The platelet testing device using blockage phenomenon according to claim 1, further comprising a stirrer rotatably arranged in the sample chamber to apply shear force to the blood sample so as to activate the platelet in the blood sample.

6. The platelet testing device using blockage phenomenon according to claim 1, wherein a platelet activating reagent, which activates the platelet in the blood sample, is contained in the sample chamber, whereby the platelet is activated in the sample chamber.

7. The platelet testing device using blockage phenomenon according to claim 1, wherein the microfluidic tube and the microbead packing are provided to have a plurality of microfluidic tubes and a plurality of microbead packings, and wherein a plurality of testing channels are formed in such a manner that each of the plurality of testing channel comprises one of the plurality of microfluidic tubes and one of the plurality of microbead packings.

8. The platelet testing device using blockage phenomenon according to claim 7, wherein one of the plurality of testing channels forms a control channel and the other of the plurality of testing channels forms a sample channel, wherein a control platelet flowing into the microbead packing of the control channel flows in a non-activated state and a sample platelet flowing into the microbead packing of the sample channel flows in an activated state.

9. The platelet testing device using blockage phenomenon according to claim 8, further comprising a stirrer rotatably arranged in the sample chamber of the sample channel to apply shear force to the blood sample so as to activate the sample platelet in the blood sample.

10. The platelet testing device using blockage phenomenon according to claim 8, wherein a platelet activating reagent, which activates the platelet in the blood sample, is contained in the sample chamber, whereby the sample platelet is activated in the sample chamber.

11. The platelet testing device using blockage phenomenon according to claim 6, wherein the platelet activating reagent comprises any one of calcium ion, adenosine diphosphate (ADP), epinephrine, arachidonic acid, thromboxane A2, thrombin, and iso-thrombin-receptor-activating peptide (iso-TRAP), or a combination thereof.

12. The platelet testing device using blockage phenomenon according to claim 1, wherein at least a portion of a surface of one of the plurality of the microbeads is shaped to be porous.

13. The platelet testing device using blockage phenomenon according to claim 1, further comprising a negative pressure inflow chamber, which is connected to the microfluidic tube at an opposite of the sample chamber and which introduces a negative pressure from outside, such that the blood sample flows through the microfluidic tube.

14. The platelet testing device using blockage phenomenon according to claim 8, wherein a degree of an activation of the platelet is determined based on at least one of travel distance of the blood sample in the sample channel, travel distance of the blood sample in the control channel, time taken for the stop of the blood sample in the sample channel, and time taken for the stop of the blood sample in the control channel, a difference of travel distance of the blood sample in the sample channel and travel distance of the blood sample in the control channel, a ratio of travel distance of the blood sample in the sample channel to travel distance of the blood sample in the control channel, a difference of time taken for the stop of the blood sample in the sample channel and time taken for the stop of the blood sample in the control channel, and a ratio of time taken for the stop of the blood sample in the sample channel to time taken for the stop of the blood sample in the control channel.

15. The platelet testing device using blockage phenomenon according to claim 1, wherein the microbead packing further comprises a mesh member, which is arranged at a rear end of the packing pipe in a flow direction of the blood sample, to prevent loss of the microbeads, and wherein the mesh member comprises a plurality of openings smaller in size than the plurality of microbeads.

16. A platelet testing device using blockage phenomenon, comprising:
a sample chamber containing a blood sample;
a microfluidic tube, which is in fluid communication with the sample chamber and through which the blood sample flows;
a microbead packing arranged on a flow path of the blood sample of the microfluidic tube; and
a stirrer rotatably arranged in the sample chamber to apply shear force to the blood sample so as to activate a platelet in the blood sample,
wherein the microbead packing comprises:
a packing pipe disposed in a portion of the microfluidic tube, separated from the sample chamber by the microfluidic tube, and constituting a part of the flow path of the blood sample; and
a plurality of microbeads contained in the packing pipe and arranged to be in close contact with each other so as to form voids between the plurality of microbeads,
whereby function of the platelet is tested by blockage phenomenon of the voids due to the platelet in the blood sample, which flows through the microfluidic tube from the sample chamber,
wherein the packing pipe is extended in parallel with an extension direction of the microfluidic tube and both ends of the packing pipe are connected to the microfluidic tube, and
wherein an inner diameter of the packing pipe is configured to be the same as an inner diameter of the microfluidic tube,
wherein the platelet in the blood sample is configured to flow into the microbead packing in an activated state in the sample chamber,
wherein a degree, to which the platelet is activated, is determined by any one of a travel distance of the blood sample, which passed through the microbead packing, and time taken for a stop of the blood sample flow, based on at least one of whether the void is blocked, a degree of the blockage of the void, and time taken for the void blockage, according to a degree to which the platelet in the blood sample is activated, and
wherein at least some of the plurality of microbeads are connected with another microbead adjacent to the at least some of the plurality of microbeads to form a plurality of fused microbeads by a fused portion of the at least some of the plurality of the microbeads and the another microbead.

17. A platelet testing device using blockage phenomenon, comprising:
a sample chamber containing a blood sample;
a microfluidic tube, which is in fluid communication with the sample chamber and through which the blood sample flows;
a microbead packing arranged on a flow path of the blood sample of the microfluidic tube; and
a negative pressure inflow chamber, which is connected to the microfluidic tube at an opposite of the sample chamber and which introduces a negative pressure from outside, such that the blood sample flows through the microfluidic tube,
wherein the microbead packing comprises:
a packing pipe disposed in a portion of the microfluidic tube, separated from the sample chamber by the microfluidic tube, and constituting a part of the flow path of the blood sample; and
a plurality of microbeads contained in the packing pipe and arranged to be in close contact with each other so as to form voids between the plurality of microbeads,
whereby function of a platelet is tested by blockage phenomenon of the voids due to the platelet in the blood sample, which flows through the microfluidic tube from the sample chamber,
wherein the packing pipe is extended in parallel with an extension direction of the microfluidic tube and both ends of the packing pipe are connected to the microfluidic tube, and
wherein an inner diameter of the packing pipe is configured to be the same as an inner diameter of the microfluidic tube,
wherein the platelet in the blood sample is configured to flow into the microbead packing in an activated state in the sample chamber,
wherein a degree, to which the platelet is activated, is determined by any one of a travel distance of the blood sample, which passed through the microbead packing, and time taken for a stop of the blood sample flow, based on at least one of whether the void is blocked, a degree of the blockage of the void, and time taken for the void blockage, according to a degree to which the platelet in the blood sample is activated, and
wherein at least some of the plurality of microbeads are connected with another microbead adjacent to the at least some of the plurality of microbeads to form a plurality of fused microbeads by a fused portion of the at least some of the plurality of the microbeads and the another microbead.

\* \* \* \* \*